US00PP18616P2

(12) United States Plant Patent
Iwaki et al.

(10) Patent No.: US PP18,616 P2
(45) Date of Patent: Mar. 18, 2008

(54) ***PETUNIA* PLANT NAMED 'SUNSURFPAFURE'**

(50) Latin Name: *Petunia×hybrida*
Varietal Denomination: Sunsurfpafure

(75) Inventors: Kazunari Iwaki, Shiga (JP); Takeshi Kanaya, Shiga (JP); Yukihiro Ikeda, Hyogo (JP); Shinya Miyano, Tounosyou-machi (JP)

(73) Assignees: Suntory Flowers Limited, Tokyo (JP); Keisei Rose Nurseries, Inc., Tokyo (JP)

( * ) Notice: Subject to any disclaimer, the term of this patent is extended or adjusted under 35 U.S.C. 154(b) by 0 days.

(21) Appl. No.: 11/527,824

(22) Filed: Sep. 27, 2006

(51) Int. Cl.
*A01H 5/00* (2006.01)

(52) U.S. Cl. ..... Plt./356

(58) Field of Classification Search ..... Plt./356
See application file for complete search history.

(56) References Cited

U.S. PATENT DOCUMENTS

PP15,756 P3 * 5/2005 Miyazaki et al. ..... Plt./356

OTHER PUBLICATIONS

UPOV ROM GTITM Computer Database, GTI Jouve Retrieval Software 2007/02 Citation for 'Sunsurfparure'.*

* cited by examiner

*Primary Examiner*—Wendy Haas
(74) *Attorney, Agent, or Firm*—C. A. Whealy

(57) ABSTRACT

A new and distinct cultivar of *Petunia* plant named 'Sunsurfpafure', characterized by its outwardly spreading to trailing and decumbent plant habit; vigorous growth habit; freely branching and flowering plant habit; long flowering period; and medium-sized red purple-colored flowers with white-colored margins.

1 Drawing Sheet

Botanical designation: *Petunia×hybrida.*
Cultivar denomination: 'Sunsurfpafure'.

BACKGROUND OF THE INVENTION

The present invention relates to a new and distinct cultivar of *Petunia,* botanically known as *Petunia×hybrida* and hereinafter referred to by the name 'Sunsurfpafure'.

The new *Petunia* is a product of a planned breeding program conducted by the Inventors in Shiga, Japan. The objective of the breeding program is to create new *Petunia* cultivars with attractive foliage shape and coloration.

The new *Petunia* originated from a cross-pollination made by the Inventors in June, 2001 in Shiga, Japan of the *Petunia×hybrida* cultivar Prime Time Burgundy Star, not patented, as the female, or seed, parent with a proprietary selection of *Petunia×hybrida* identified as code number Y-1, not patented, as the male, or pollen, parent. The new *Petunia* was discovered and selected by the Inventors as a single flowering plant within the progeny of the stated cross-pollination in a controlled environment in Shiga, Japan.

Asexual reproduction of the new *Petunia* by terminal cuttings in a controlled environment in Shiga, Japan since September, 2003, has shown that the unique features of this new *Petunia* are stable and reproduced true to type in successive generations.

SUMMARY OF THE INVENTION

The cultivar Sunsurfpafure has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Sunsurfpafure'. These characteristics in combination distinguish 'Sunsurfpafure' as a new and distinct cultivar of *Petunia:*

1. Outwardly spreading to trailing and decumbent plant habit.
2. Vigorous growth habit.
3. Freely branching and flowering plant habit.
4. Long flowering period.
5. Medium-sized red purple-colored flowers with white-colored margins.

Plants of the new *Petunia* can be compared to plants of the female parent, the cultivar Prime Time Burgundy Star. Plants of the new *Petunia* differ from plants of the cultivar Prime Time Burgundy Star in the following characteristics:

1. Plants of the new *Petunia* are more decumbent than and not as upright as plants of the cultivar Prime Time Burgundy Star.
2. Plants of the new *Petunia* have larger flowers than plants of the cultivar Prime Time Burgundy Star.
3. Plants of the new *Petunia* and the cultivar Prime Time Burgundy Star differ in flower color.

Plants of the new *Petunia* can be compared to plants of the male parent selection. Plants of the new *Petunia* differ primarily from plants of the male parent selection in the following characteristics:

1. Plants of the new *Petunia* have smaller flowers than plants of the male parent selection.
2. Plants of the new *Petunia* and the male parent selection differ in flower color.

Plants of the new *Petunia* can also be compared to plants of the cultivar Baccarat Blue Picotee, not patented. In side-by-side comparisons conducted in Shiga, Japan, plants of the new *Petunia* and the cultivar Baccarat Blue Picotee differed in the following characteristics:

1. Plants of the new *Petunia* were more decumbent than and not as upright as plants of the cultivar Baccarat Blue Picotee.
2. Plants of the new *Petunia* were broader than plants of the cultivar Baccarat Blue Picotee.
3. Plants of the new *Petunia* were more freely branching than plants of the cultivar Baccarat Blue Picotee.
4. Plants of the new *Petunia* had larger leaves than plants o the cultivar Baccarat Blue Picotee.
5. Plants of the new *Petunia* were more freely flowering than plants of the cultivar Baccarat Blue Picotee.
6. Plants of the new *Petunia* and the cultivar Baccarat Blue Picotee differed in flower color.

BRIEF DESCRIPTION OF THE PHOTOGRAPHS

The accompanying color photographs illustrate the overall appearance of the new *Petunia,* showing the colors as true as it is reasonably possible to obtain in colored reproductions of this type. Colors in the photographs may differ slightly from the color values cited in the detailed botanical description which accurately describe the colors of the new *Petunia.*

The photograph at the top of the sheet comprises a side perspective view of a typical flowering plant of 'Sunsurfapafure' grown in a container.

The photograph at the bottom of the sheet comprises a close-up of typical flowers and leaves of 'Sunsurfpafure'.

DETAILED BOTANICAL DESCRIPTION

The photographs and following observations, measurements and values describe plants grown in Shiga, Japan, under commercial practice during the spring in an outdoor nursery day temperatures averaging 23° C. and night temperatures averaging 13° C. Plants were grown for about four months with one plant per 13.5-cm container. In the following description, color references are made to The Royal Horticultural Society Colour Chart, 2001 Edition, except where general terms of ordinary dictionary significance are used.

Botanical classification: *Petunia×hybrida* cultivar Sunsurfpafure.

Parentage:

*Female, or seed, parent.*—*Petunia×hybrida* cultivar Prime Time Burgundy Star, not patented.

*Male, or pollen, parent.*—Proprietary selection of *Petunia×hybrida* identified as code number Y-1, not patented.

Propagation:

*Type.*—By terminals cuttings.

*Time to initiate roots.*—About one week at temperatures of 20° C. to 25° C.

*Time to produce a rooted young plant.*—About three weeks at temperatures of 20° C. to 25° C.

*Root description.*—Fine, fibrous; light brown in color.

*Rooting habit.*—Freely branching.

Plant description:

*Plant and growth habit.*—Outwardly spreading to trailing and decumbent plant habit. Freely branching with about 18 lateral branches per plant; pinching enhances lateral branch development. Vigorous growth habit.

*Plant height.*—About 14.8 cm.

*Plant diameter.*—About 44.2 cm.

Lateral branch description:

*Length.*—About 18.8 cm.

*Diameter.*—About 2.5 mm.

*Internode length.*—About 2.6 cm.

*Strength.*—Strong.

*Aspect.*—Initially upright to trailing and decumbent.

*Texture.*—Pubescent.

*Color.*—144A.

Foliage description:

*Arrangement.*—Before flowering, alternate, simple; after flowering, opposite, simple.

*Length.*—About 6.2 cm.

*Width.*—About 2.7 cm.

*Shape.*—Elliptic.

*Apex.*—Obtuse.

*Base.*—Cuneate.

*Margin.*—Entire.

*Texture, upper and lower surfaces.*—Pubescent.

*Venation pattern.*—Pinnate; reticulate.

*Color.*—Developing and fully expanded foliage, upper surface: 138A; venation, 145B. Developing and fully extended foliage, lower surface: 146B; venation, 145B.

*Petiole.*—Length: About 4.4 mm. Diameter: About 1.4 mm. Texture, upper and lower surfaces: Pubescent. Color, upper and lower surfaces: 144C.

Flower description:

*Flower arrangement and habit.*—Single salverform flowers arising from leaf axils. Freely flowering habit with usually about 54 flowers developing per plant. Flowers not persistent. Flowers face upright or outwardly.

*Fragrance.*—Faint; sweet.

*Natural flowering season.*—Plants of the new *Petunia* initiate and develop flowers about two or three weeks after planting. Long flowering period; flowering commences naturally during the spring and plants flower continuously throughout the summer until the fall in Japan.

*Flower longevity.*—Individual flowers last about five days on the plant.

*Flower diameter.*—About 7.2 cm.

*Flower length (depth).*—About 4.1 cm.

*Throat diameter.*—About 1.1 cm.

*Tube diameter.*—About 3.1 mm.

*Flower bud.*—Shape: Elongated oblong. Length: About 4.4 cm. Diameter: About 6.5 mm. Color: N79A.

*Corolla.*—Arrangement: Five petals fused at the base and opening into a flared trumpet. Petal length from throat: About 2.9 cm. Petal width: About 3.1 cm. Petal shape: Broadly obovate. Petal apex: Pointed. Petal margin: Entire; slightly undulate. Petal texture, upper and lower surfaces: Smooth, glabrous; satiny. Tube texture: Pubescent. Color: Petal, when opening and fully opened, upper surface: Close to 74A; towards the margins, 155D; venation, N79A. Petal, when opening and fully opened, lower surface: 77B; venation, similar to lamina. Throat: N87A; venation, N79A. Tube: 79B; venation, 79B.

*Calyx.*—Arrangement: One star-shaped calyx tube with five sepals fused at the base per flower. Sepal length: About 1.7 cm. Sepal width: About 4.6 mm. Sepal shape: Narrowly elliptic. Sepal apex: Rounded. Sepal margin: Entire. Sepal texture, upper and lower surfaces: Pubescent. Color, upper and lower surfaces: 144A.

*Peduncles.*—Length: About 3.1 cm. Diameter: About 1.3 mm. Angle: About 45° from vertical. Strength: Strong. Texture: Pubescent; viscid. Color: 144A.

*Reproductive organs.*—Stamens: Quantity/arrangement: Five per flower. Anther shape: Ellipsoidal. Anther length: About 2 mm. Anther color: N88C. Pollen amount: Moderate. Pollen color: 94B. Pistils: Quantity: One per flower. Pistil length: About 1.6 cm. Style color: 144D. Stigma shape: Transversely ellipsoidal. Stigma color: 83A. Ovary color: 144A. Seed/fruit: Seed and fruit development have not been observed on plants of the new *Petunia*.

Temperature tolerance: Plants of the new *Petunia* have been observed to tolerate temperatures from about 5° C. to about 35° C.

Pathogen/pest resistance: Plants of the new *Petunia* have not been observed to be resistant to pests and pathogens common to *Petunia*.

It is claimed:

1. A new and distinct *Petunia* plant named 'Sunsurfpafure' as illustrated and described.

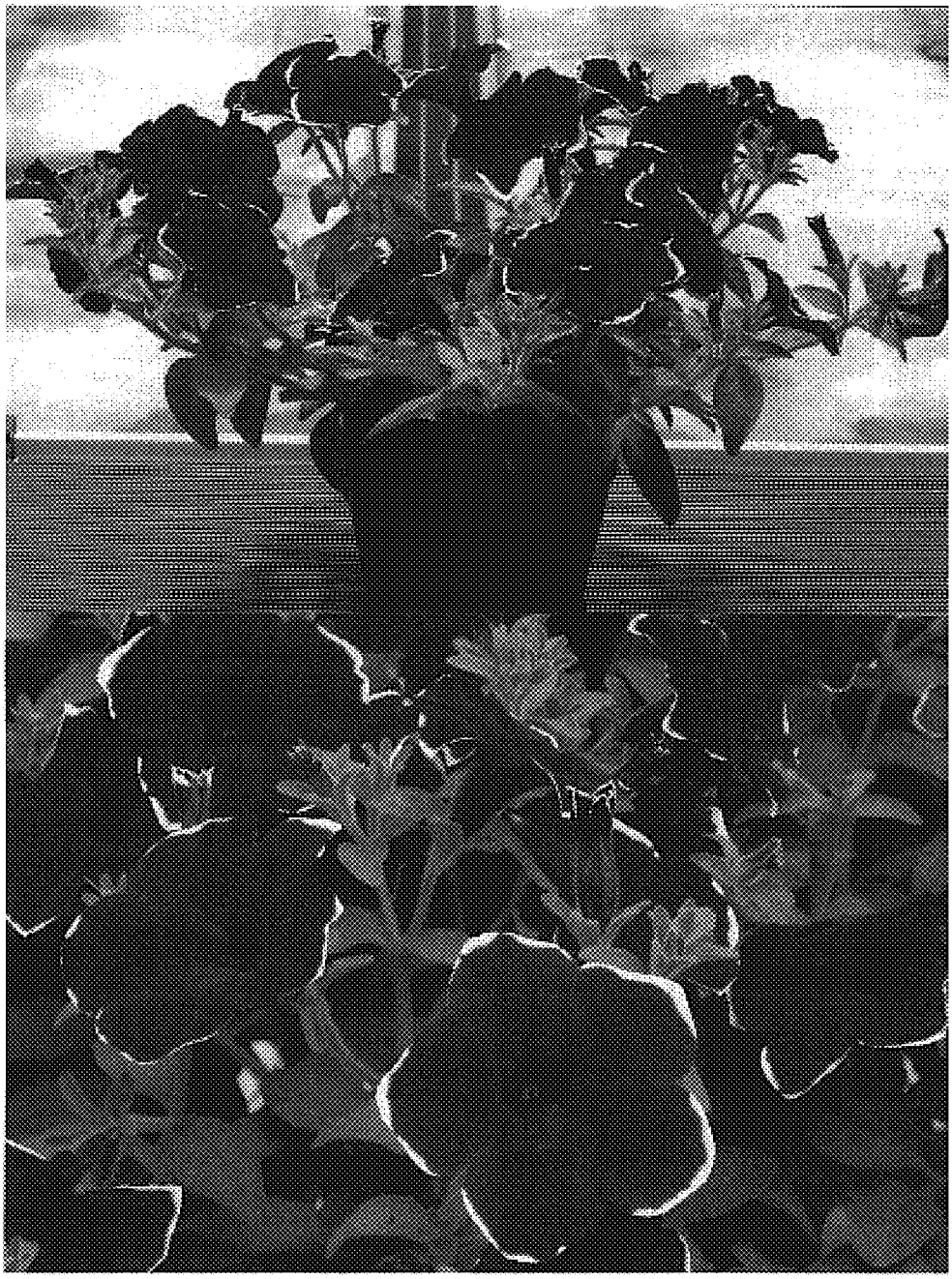

* * * * *